(12) United States Patent
Zhang et al.

(10) Patent No.: US 10,463,561 B2
(45) Date of Patent: Nov. 5, 2019

(54) WEARABLE DEVICE AND CONTROL METHOD THEREOF

(71) Applicant: BOE TECHNOLOGY GROUP CO., LTD., Beijing (CN)

(72) Inventors: Ying Zhang, Beijing (CN); Zhongcheng Gui, Beijing (CN); Yifei Zhang, Beijing (CN); Kai Zhao, Beijing (CN); Yu Gu, Beijing (CN); Hongli Ding, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 0 days.

(21) Appl. No.: 15/326,590

(22) PCT Filed: Jul. 20, 2016

(86) PCT No.: PCT/CN2016/090624
§ 371 (c)(1),
(2) Date: Jan. 16, 2017

(87) PCT Pub. No.: WO2017/076065
PCT Pub. Date: May 11, 2017

(65) Prior Publication Data
US 2018/0228683 A1    Aug. 16, 2018

(30) Foreign Application Priority Data
Nov. 5, 2015    (CN) .......................... 2015 1 0750216

(51) Int. Cl.
*A61H 1/02* (2006.01)
*A61H 3/00* (2006.01)
(Continued)

(52) U.S. Cl.
CPC ......... *A61H 1/0237* (2013.01); *A61B 5/1071* (2013.01); *A61B 5/112* (2013.01);
(Continued)

(58) Field of Classification Search
CPC ..... A61B 5/1071; A61B 5/112; A61H 1/0237; A61H 1/0262; A61H 2003/007; A61H 3/00; B25J 9/0006
See application file for complete search history.

(56) References Cited

U.S. PATENT DOCUMENTS 8,674,838 B2 *  3/2014  Konishi ................. A61H 3/008
                                                  340/539.12
8,905,955 B2    12/2014  Goffer et al.
(Continued)

FOREIGN PATENT DOCUMENTS

CN       101242797 A    8/2008
CN       101273946 A    10/2008
(Continued)

OTHER PUBLICATIONS

Second Office Action for Chinese Application No. 201510750216.4, dated Aug. 15, 2017, 9 Pages.
(Continued)

*Primary Examiner* — Brian A Dukert
(74) *Attorney, Agent, or Firm* — BROOKS KUSHMAN P.C.

(57) ABSTRACT

The wearable device provided by embodiments of the present disclosure is used for enhancing physical fitness, and includes a first connection member, a second connection member, a first joint member, a second joint member, a first fixing structure, a second fixing structure, a third fixing structure, a first sensor and a first controller. According to embodiments of the present disclosure, motion control may be implemented by obtaining a motion state parameter of an arm of the user and controlling, according to the motion statement parameter, the first connection member and the (Continued)

second connection member to act, so that the user may adjust his walking speed and stride naturally and conveniently.

17 Claims, 6 Drawing Sheets

(51) Int. Cl.
*A61B 5/107* (2006.01)
*A61B 5/11* (2006.01)
*A61B 5/00* (2006.01)

(52) U.S. Cl.
CPC .......... *A61B 5/1121* (2013.01); *A61B 5/6824* (2013.01); *A61H 1/024* (2013.01); *A61H 1/0244* (2013.01); *A61B 2562/0219* (2013.01); *A61H 3/00* (2013.01); *A61H 2003/007* (2013.01); *A61H 2201/0157* (2013.01); *A61H 2201/164* (2013.01); *A61H 2201/165* (2013.01); *A61H 2201/5007* (2013.01); *A61H 2201/5069* (2013.01); *A61H 2201/5084* (2013.01)

(56) References Cited

U.S. PATENT DOCUMENTS

| | | | |
|---|---|---|---|
| 2009/0131839 | A1 | 5/2009 | Yasuhara |
| 2010/0036302 | A1 | 2/2010 | Shimada et al. |
| 2012/0101415 | A1* | 4/2012 | Goffer .................. A61H 1/024 601/35 |
| 2013/0231595 | A1 | 9/2013 | Zoss et al. |
| 2015/0190923 | A1 | 7/2015 | Seo et al. |

FOREIGN PATENT DOCUMENTS

| | | |
|---|---|---|
| CN | 102036638 A | 4/2011 |
| CN | 102176886 A | 9/2011 |
| CN | 103153356 A | 6/2013 |
| CN | 103328051 A | 9/2013 |
| CN | 103330635 A | 10/2013 |
| CN | 103622792 A | 3/2014 |
| CN | 203483748 U | 3/2014 |
| CN | 103932868 A | 7/2014 |
| CN | 103932872 A | 7/2014 |
| CN | 104188675 A | 12/2014 |
| CN | 104490563 A | 4/2015 |
| CN | 104552276 A | 4/2015 |
| CN | 104666047 A | 6/2015 |
| CN | 105213156 A | 1/2016 |
| CN | 205094946 U | 3/2016 |
| JP | 2006075456 A | 3/2006 |
| JP | 2011206366 A | 10/2011 |
| WO | 2011002306 A1 | 1/2011 |

OTHER PUBLICATIONS

Chinese First Office Action for Chinese Application No. 201510750216.4, dated Dec. 5, 2016, 8 Pages.
International Search Report and Written Opinion for Application No. PCT/CN2016/090624, dated Jul. 20, 2016, 13 Pages.
Third Office Action for Chinese Application No. 201510750216.4, dated Mar. 6, 2018, 10 Pages.

* cited by examiner

WEARABLE DEVICE AND CONTROL METHOD THEREOF

CROSS-REFERENCE TO RELATED APPLICATIONS

This application is the U.S. national phase of PCT Application No. PCT/CN2016/090624 filed on Jul. 20, 2016, which claims priority to Chinese Patent Application No. 201510750216.4 filed on Nov. 5, 2015, the disclosures of which are incorporated in their entirety by reference herein.

TECHNICAL FIELD

The present disclosure relates to the field of artificial intelligence technology, particularly to a wearable device and a control method thereof, and more particularly to powered exoskeleton and a control method thereof.

BACKGROUND

Power exoskeleton is a wearable device which can enhance physical fitness and can be driven by a hydraulic or pneumatic system. The power exoskeleton is used to improve or enhance the body's physiological function, mainly to improve the body's limbs movement ability, especially strength and endurance. It can help people run faster, jump higher, can carry more and heavier things, and help people wear it in the battlefield, construction sites or other dangerous places to survive.

Currently, the power exoskeleton has two major applications. One is a military application, in which soldiers who wear the exoskeleton can load heavier weapons and equipment, and can also walk with loading for a longer time, so as to improve combat capability of the soldiers. The other is a civil application, especially for the disabled or the elderly, which can help them have normal or even extraordinary physiological functions, especially walking ability. However, the existing power exoskeleton structure is complex, and has a higher demand on the user's operation capability, which results in clumsy operations of the existing power exoskeleton and a narrower application range.

BRIEF DESCRIPTION

I. Technical Problem to be Solved

In order to solve the above problems, the present disclosure provides a wearable device (for example, power exoskeleton) and a control method thereof for solving the problems with the conventional solutions that the existing power exoskeleton structure is complex, and has a higher demand on the user's operation capability, which results in clumsy operations of the existing power exoskeleton and a narrower application range.

II. Technical Solutions

For this purpose, in a first aspect, an embodiment of the present disclosure provides a wearable device for enhancing physical fitness, which includes a first connection member, a second connection member, a first joint member, a second joint member, a first fixing structure, a second fixing structure, a third fixing structure, a first sensor and a first controller. The first connection member and the second connection member are connected by the second joint member. The first fixing structure and the first connection member are connected by the first joint member. The second fixing member is connected to the first connection member. The third fixing structure is connected to the second connection member. The first fixing structure is used to be fixed at a waist of a user so as to fix the first joint member at the waist of the user. The second fixing structure is used to be fixed at a thigh of the user so as to fix the first connection member at the thigh of the user. The third fixing structure is used to be fixed at a shank of the user so as to fix the second connection member at the shank of the user. The first sensor is used to obtain a motion state parameter of an arm of the user. The first controller is used to control, according to the motion statement parameter, the first connection member and the second connection member to act, so as to drive the thigh and the shank to act.

In a possible embodiment, the wearable device is power exoskeleton.

In a possible embodiment, the motion state parameter includes a swing amplitude of the arm and an elbow joint angle between an upper arm and a forearm.

In a possible embodiment, the motion state parameter further includes a swing frequency of the arm.

In a possible embodiment, the first connection member includes a thigh connection rod, and the second connection member includes a shank connection rod.

In a possible embodiment, the first joint member includes a first driver and a hip joint, and the second joint member includes a second driver and a knee joint.

In a possible embodiment, the wearable device further includes: a foot support member, a third joint member and a fourth fixing structure. The foot support member is connected to the second connection member by the third joint member, and the fourth fixing structure is connected to the foot support member. The fourth fixing structure is used to be fixed at a foot of the user, so as to fix the foot support member at the foot of the user. The first controller is used to control, according to the motion state parameter, the foot support member to act, so as to drive the foot to act.

In a possible embodiment, the third joint member may include a third driver and an ankle joint.

In a possible embodiment, the first sensor may include an acceleration meter, a data processor and an angle meter. The acceleration meter is used to measure an angle acceleration between the upper arm and a middle axis of body. The data processor is used to calculate the swing amplitude and the swing frequency of the arm according to the angle acceleration. The angle meter is used to measure the elbow joint angle between the upper arm and the forearm.

In a possible embodiment, the first sensor may be arranged at the elbow joint of the user.

In a second aspect, an embodiment of the present disclosure further provides a method for controlling a wearable device, the wearable device being used for enhancing physical fitness and including a first connection member, a second connection member, a first joint member, a second joint member, a first fixing structure, a second fixing structure, a third fixing structure, a first sensor and a first controller. The first connection member and the second connection member are connected by the second joint member. The first fixing structure and the first connection member are connected by the first joint member. The second fixing member is connected to the first connection member. The third fixing structure is connected to the second connection member. The first fixing structure is used to be fixed at a waist of a user so as to fix the first joint member at the waist of the user. The second fixing structure is used to be fixed at a thigh of the user so as to fix the first connection member at the thigh of the user. The third fixing structure is used to be fixed at a shank of the user so as to fix the second connection member at the shank of the user. The method includes: obtaining, by the first sensor, a motion state parameter of an arm of the user; and controlling, by the first controller according to the motion statement parameter, the first connection member and the second connection member to act, so as to drive the thigh and the shank to act.

In a possible embodiment, the wearable device is power exoskeleton.

In a possible embodiment, when the arm of the user is in a periodical motion state, the step of controlling, by the first controller according to the motion statement parameter, the first connection member and the second connection member to act may include: controlling, by the first controller according to the motion statement parameter of the arm of the user after at least one motion cycle, the first connection member and the second connection member to act, so as to enable actions of the thigh and the shank to be delayed by at least one motion cycle relative to the action of the arm.

In a possible embodiment, before the step of obtaining, by the first sensor, the motion state parameter of the arm of the user, the control method further includes: enabling the arm of the user to keep natural prolapse for a predetermined time, so as to initialize the wearable device.

In a possible embodiment, the step of obtaining, by the first sensor, the motion state parameter of the arm of the user may include: obtaining, by the first sensor, a swing amplitude of the arm and an elbow joint angle between an upper arm and a forearm. The step of controlling, by the first controller according to the motion statement parameter, the first connection member and the second connection member to act may include: determining whether the swing amplitude is larger than a first predetermined threshold; determining whether the elbow joint angle is larger than a second predetermined threshold, if the swing amplitude is larger than the first predetermined threshold; controlling, by the first controller, the first connection member and the second connection member to act so as to enable the user to be in a walking mode, if the elbow joint angle is smaller than the second predetermined threshold; and controlling, by the first controller, the first connection member and the second connection member to act so as to enable the user to be in a running mode, if the elbow joint angle is larger than the second predetermined threshold.

In a possible embodiment, the step of obtaining, by the first sensor, the motion state parameter of the arm of the user may include: obtaining, by the first sensor, a swing amplitude of the arm and an elbow joint angle between an upper arm and a forearm. The step of controlling, by the first controller according to the motion statement parameter, the first connection member and the second connection member to act may include: determining whether the swing amplitude is larger than a first predetermined threshold; determining whether the elbow joint angle is larger than a second predetermined threshold, if the swing amplitude is larger than the first predetermined threshold; controlling, by the first controller, the first connection member and the second connection member to act so as to enable the user to be in a walking mode, if the elbow joint angle is smaller than the second predetermined threshold; and controlling, by the first controller, the first connection member and the second connection member to act so as to enable the user to be in a running mode, if the elbow joint angle is larger than the second predetermined threshold.

In a possible embodiment, the step of obtaining, by the first sensor, the motion state parameter of the arm of the user may include: obtaining, by the first sensor, a first swing amplitude $\alpha_{L(i-1)}$ of a left arm in an (i−1)-th motion cycle and a second swing amplitude $\alpha_{R(i-1)}$ of a right arm in the (i−1)-th motion cycle. The step of controlling, by the first controller according to the motion statement parameter, the first connection member and the second connection member to act may include: controlling, by the first controller according to the first swing amplitude $\alpha_{L(i-1)}$ and the second swing amplitude $\alpha_{R(i-1)}$, a step length of lower limbs in an i-th motion cycle as $STEP\alpha_i = K\alpha_i * STEP\alpha_M$, in which a proportion coefficient $K\alpha_i = (\alpha_{L(i-1)} + \alpha_{R(i-1)})/(2\alpha_M)$, $\alpha_M$ is a predetermined maximum swing amplitude of upper limbs, $STEP\alpha_M$ is a predetermined maximum step length of the lower limbs; and when the obtained proportion coefficient $K\alpha_i$ is larger than 1, the proportion coefficient $K\alpha_i$ is set to be 1 so that the proportion coefficient $K\alpha_i$ is no more than 1.

In a possible embodiment, the step of obtaining, by the first sensor, the motion state parameter of the arm of the user may include: obtaining, by the first sensor, a first swing frequency $\gamma_{L(i-1)}$ of a left arm in an (i−1)-th motion cycle and a second swing frequency $\gamma_{R(i-1)}$ of a right arm in the (i−1)-th motion cycle. Te step of controlling, by the first controller according to the motion statement parameter, the first connection member and the second connection member to act may include: controlling, by the first controller according to the first swing frequency $\gamma_{L(i-1)}$ and the second swing frequency $\gamma_{R(i-1)}$, a frequency of lower limbs in an i-th motion cycle as $STEP\gamma_i = K\gamma_i * STEP\gamma_M$, in which a proportion coefficient $K\gamma_i = (\gamma_{L(i-1)} + \gamma_{R(i-1)})/(2\gamma_M)$, $\gamma_M$ is a predetermined maximum swing frequency of upper limbs, $STEP\gamma_M$ is a predetermined maximum frequency of the lower limbs; and when the obtained proportion coefficient $K\gamma_i$ is larger than 1, the proportion coefficient $K\gamma_i$ is set to be 1 so that the proportion coefficient $K\gamma_i$ is no more than 1.

In a possible embodiment, the wearable device may further include: a foot support member, a third joint member and a fourth fixing structure. The foot support member is connected to the second connection member by the third joint member. The fourth fixing structure is connected to the foot support member. The fourth fixing structure is used to be fixed at a foot of the user, so as to fix the foot support member at the foot of the user. The control method may further include: controlling, by the first controller according to the motion state parameter, the foot support member to act, so as to drive the foot to act.

In a possible embodiment, the first sensor includes at least one of an acceleration meter, a data processor and an angle meter. The step of obtaining, by the first sensor, the motion state parameter of the arm of the user may include: measuring, by the acceleration meter, an angle acceleration between the upper arm and a middle axis of body; calculating, by the data processor, the swing amplitude and the swing frequency of the arm according to the angle acceleration; and measuring, by the angle meter, the elbow joint angle between the upper arm and the forearm.

III. Beneficial Effects

The embodiments of the present disclosure have at least beneficial effects as follows.

According to the wearable device (power exoskeleton) and the control method thereof, the wearable device (power exoskeleton) includes a first connection member, a second connection member, a first joint member, a second joint member, a first fixing structure, a second fixing structure, a third fixing structure, a first sensor and a first controller. The first sensor obtains the motion state parameter of the arm of the user; the first controller controls, according to the motion statement parameter, the first connection member and the second connection member to act, so as to drive the thigh and the shank to act. In the embodiments of the present disclosure, the motion state parameter of the arm of the user is obtained; and according to the motion state parameter, the first connection member and the second connection member are controlled to act for implementing motion control, so that the user can adjust his walking speed and stride naturally and conveniently. Technical solutions according to the embodiments of the present disclosure may provide simple structures, require a lower demand on operation capability of the user, and have higher operation flexibility. In addition, the technical solutions according to the embodiments of the present disclosure may be applied to the user whose lower limbs completely lose their movement functions, as long as the arms of the user have normal functions, which thus have a broader application range.

BRIEF DESCRIPTION OF THE DRAWINGS

In order to illustrate the technical solutions of the present disclosure or the related art in a more apparent manner, the drawings desired for the embodiments of the present disclosure will be described briefly hereinafter. Obviously, the following drawings merely relate to some embodiments of the present disclosure, and based on these drawings, a person skilled in the art may obtain the other drawings without any creative effort.

DETAILED DESCRIPTION

Hereinafter, particular implementations of the present disclosure will be described in detail in conjunction with the drawings and the embodiments. The following embodiments are only used for explaining the present disclosure, but do not limit the scope of the present disclosure.

In order to make the objects, the technical solutions and the advantages of the present disclosure more apparent, the present disclosure will be described hereinafter in a clear and complete manner in conjunction with the drawings and embodiments. Obviously, the following embodiments are merely a part of, rather than all of, the embodiments of the present disclosure. And based on these embodiments, a person skilled in the art may obtain the other embodiments, which also fall within the scope of the present disclosure.

Unless otherwise defined, any technical or scientific terms used herein shall have the common meaning understood by a person of ordinary skills. Such words as "first" and "second" used in the specification and claims are merely used to differentiate different components rather than to represent any order, number or importance. Also, the references, such as "a" or "an", do not mean quantity limitation, but represent at least one. The terms, such as "connection" or "connecting", are not limited a physical or mechanical connection, but may include an electrical connection, whether direct or indirect. The terms, such as "upper", "lower", "right", "left", are merely used to represent a relative position relationship. when an absolute position of the described object is changed, the relative position relationship is changed accordingly.

In order for the skilled in the art to better understand the technical solutions of the present disclosure, the power exoskeleton and the control method thereof provided by the present disclosure will be described hereinafter in detail in connection with the drawings.

First Embodiment

Figure 1:
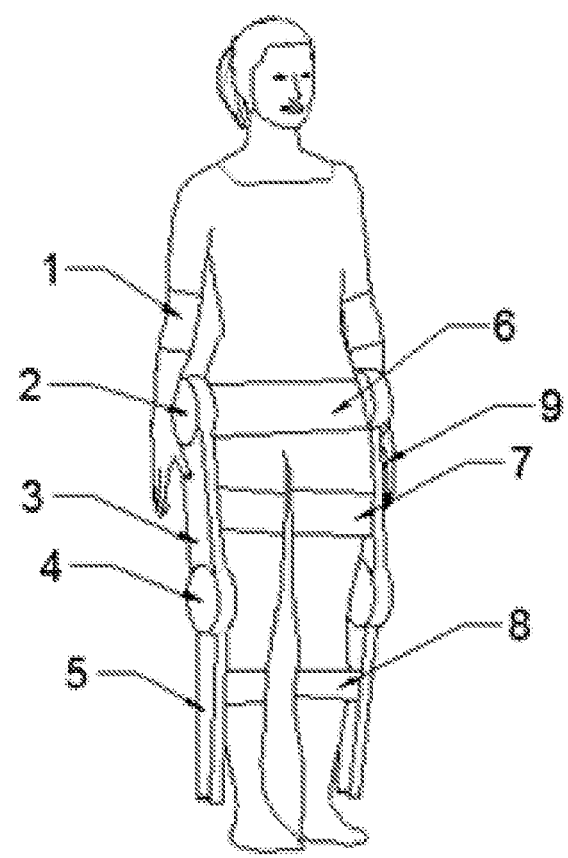
FIG. 1 is a schematic diagram illustrating a structure of power exoskeleton provided by a first embodiment of the present disclosure.

FIG. 1 is a schematic diagram illustrating a structure of a wearable device (i.e., power exoskeleton) provided by the first embodiment of the present disclosure. As shown in FIG. 1, the power exoskeleton includes a first connection member 3, a second connection member 5, a first joint member 2, a second joint member 4, a first fixing structure 6, a second fixing structure 7, a third fixing structure 8, a first sensor 1 and a first controller 9. The first connection member 3 and the second connection member 5 are connected by the second joint member 4, the first fixing structure 6 and the first connection member 3 are connected by the first joint member 2, the second fixing member 7 is connected to the first connection member 3, and the third fixing structure 8 is connected to the second connection member 5. Alternatively, the first sensor 1 is arranged at an elbow joint of a user, and the first controller 9 is a wireless handheld device.

The first fixing structure 6 is fixed at a waist of the user, so as to fix the first joint member 2 at the waist of the user. In addition, the second fixing structure 7 is fixed at a thigh of the user, so as to fix the first connection member 3 at the thigh of the user. The third fixing structure 8 is fixed at a shank of the user, so as to fix the second connection member 5 at the shank of the user. Alternatively, the fixing structure is a bandage. Of course, the fixing structure may also be other fixed molding and ergonomic structures, such as a metal or plastic snap. Accordingly in the present embodiment, the first joint member 2, the first connection member 3 and the second connection member 5 are fixed at corresponding parts of the user's body by the bandages.

The first sensor 1 is used to obtain a motion state parameter of an arm of the user, the first controller 9 is used to control, according to the motion statement parameter, the first connection member 2 and the second connection member 4 to act, so as to drive the thigh and the shank to act. In addition, the first controller 9 is further used to control to enable and disable the power exoskeleton.

Preferably, the power exoskeleton further includes a foot support member, a third joint member and a fourth fixing structure (not shown). Particularly, the foot support member is connected to the second connection member by the third joint member, and the fourth fixing structure is connected to the foot support member. The fourth fixing structure is used to be fixed at a foot of the user, so as to fix the foot support member at the foot of the user. The first controller is used to control, according to the motion state parameter, the foot support member to act, so as to drive the foot to act. In actual applications, the foot support member may also be fixed at the foot of the user by the bandage. Of course, the fixing structure for fixing the foot support member at the user's foot may also be other fixed molding and ergonomic structures, such as a metal or plastic snap.

In the present embodiment, the first connection member 3 includes a thigh connection rod, and the second connection member 5 includes a shank connection rod. The first joint member 2 includes a first driver and a hip joint, the second joint member 4 includes a second driver and a knee joint, and the third joint member includes a third driver and an ankle joint.

Figure 2:
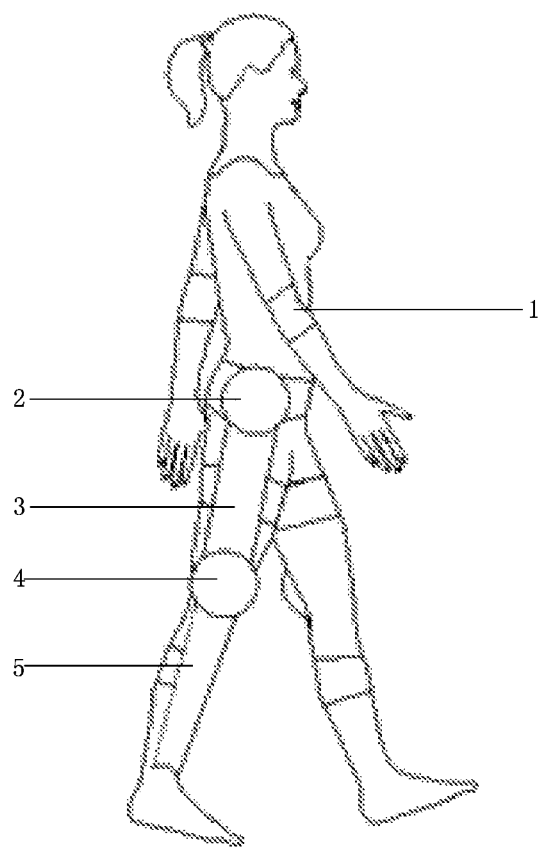
FIG. 2 is a walking state diagram of the power exoskeleton in the first embodiment of the present disclosure.
Figure 3:
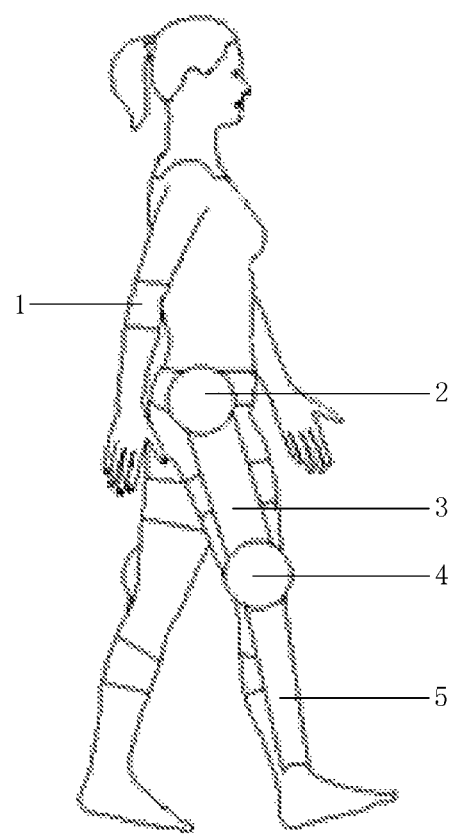
FIG. 3 is another walking state diagram of the power exoskeleton in the first embodiment of the present disclosure.

FIG. 2 is a walking state diagram of the power exoskeleton in the first embodiment. FIG. 3 is another walking state diagram of the power exoskeleton in the first embodiment. As shown in FIG. 2 and FIG. 3, in the walking mode, the power exoskeleton acts based on a preset human walking gait cycle. For example, the first driver rotates forward to raise the thigh, the second driver rotates backward to bring the shank to be vertical to the ground, and the third driver rotates to cause a sole of foot from contacting the ground by a tiptoe to contacting the ground by the whole sole, or from leaving the ground by a heel to leaving the ground by the whole sole.

Figure 4:
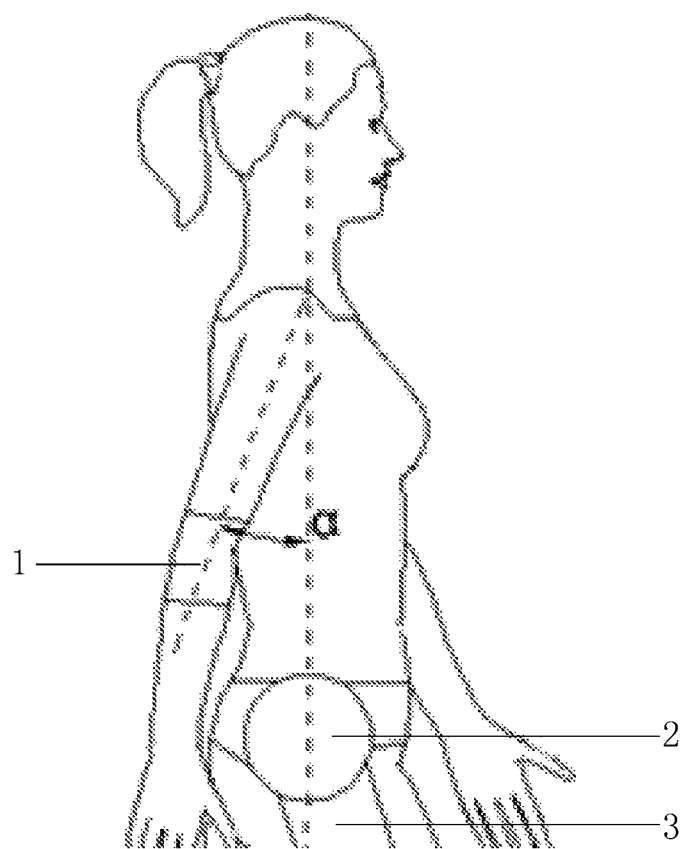
FIG. 4 is a schematic diagram illustrating a swing amplitude of the power exoskeleton in the first embodiment of the present disclosure.
Figure 5:
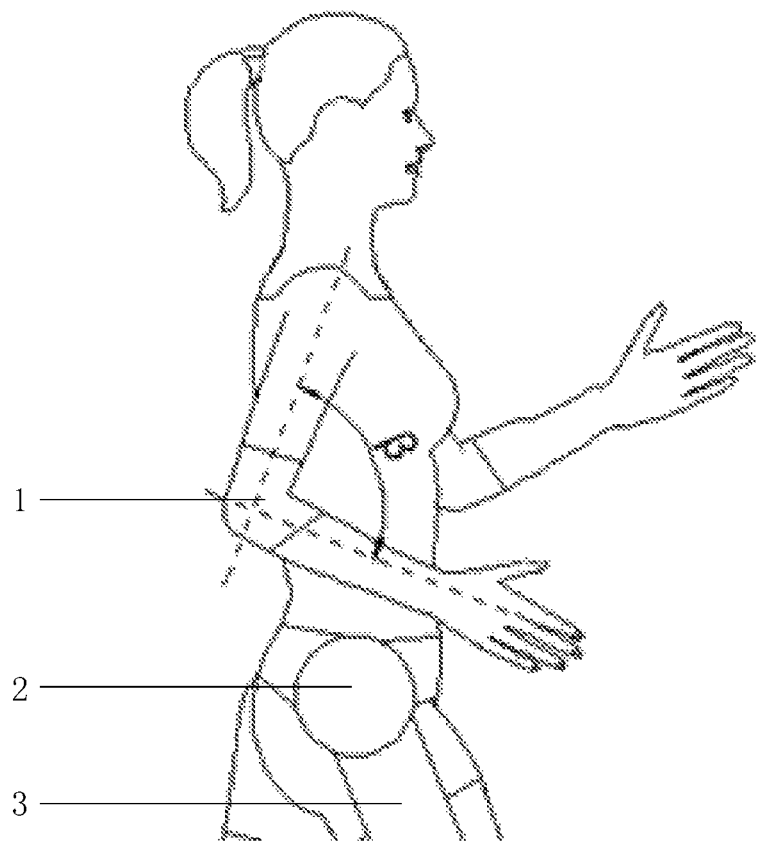
FIG. 5 is a schematic diagram illustrating an elbow joint angle of the power exoskeleton in the first embodiment of the present disclosure.

In the present embodiment, the motion state parameter includes a swing amplitude of the arm and an elbow joint angle between an upper arm and a forearm. Alternatively, the motion state parameter further comprises a swing frequency of the arm. FIG. 4 is a schematic diagram illustrating a swing amplitude of the power exoskeleton in the first embodiment. As shown in FIG. 4, the swing amplitude of the power exoskeleton is represented as a first angle $\alpha$. The first angle $\alpha$ is an angle formed between the upper arm and a middle axis of body when the arm swings forward or backward. FIG. 5 is a schematic diagram illustrating an elbow joint angle of the power exoskeleton in the first embodiment. As shown in FIG. 5, the elbow joint angle of the power exoskeleton is represented as a second angle $\beta$. The second angle $\beta$ is an angle between the upper arm and the forearm when the elbow angle is bent.

Preferably, the first sensor includes any one of an acceleration meter, a data processor and an angle meter. The acceleration meter measures an angle acceleration between the upper arm and the middle axis of body, the data processor calculates the swing amplitude and the swing frequency of the arm according to the angle acceleration, and the angle meter measures the elbow joint angle between the upper arm and the forearm. The first sensors 1 are fixed at the elbow joints of left and right sides of the body. The acceleration meter may be an accelerometer or a gyroscope. The angle meter may be a tension meter for measuring the angle between the upper arm and the forearm. A magnitude of the tension generated when the elbow joint is bent reflects a bending degree of the elbow joint, i.e., the elbow joint angle. Alternatively, the first sensor further includes a radio module for transmitting measurement information to the first controller, the measurement information including the swing amplitude, the swing frequency, the elbow joint angle, and so forth.

Therefore, the power exoskeleton provided by the present embodiment includes a first connection member, a second connection member, a first joint member, a second joint member, a first fixing structure, a second fixing structure, a third fixing structure, a first sensor and a first controller. The first sensor obtains the motion state parameter of the arm of the user; the first controller controls, according to the motion statement parameter, the first connection member and the second connection member to act, so as to drive the thigh and the shank to act. In the present embodiment, the motion state parameter of the arm of the user is obtained; and according to the motion state parameter, the first connection member and the second connection member are controlled to act for implementing motion control, so that the user can adjust his walking speed and stride naturally and conveniently. The technical solution provided by the embodiment has a simple structure, requires a lower demand on operation capability of the user, and has higher operation flexibility. In addition, the technical solution provided by the present embodiment may be applied to the user whose lower limbs completely lose their movement functions, as long as the arms of the user have normal functions, which thus have a broader application range.

Second Embodiment

Figure 6:
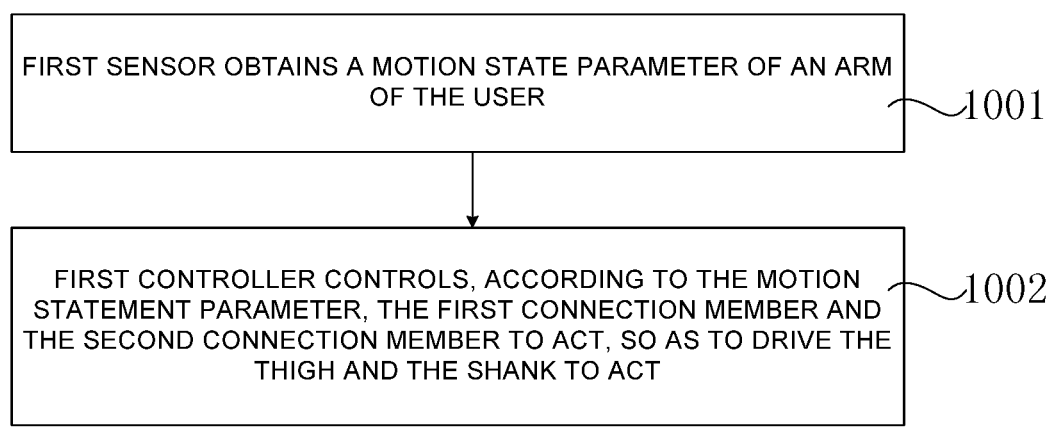
FIG. 6 is a flowchart of a control method of power exoskeleton provided by a second embodiment of the present disclosure.

FIG. 6 is a flowchart of a control method of a wearable device (i.e., power exoskeleton) provided by a second embodiment of the present disclosure. As shown in FIG. 6, the power exoskeleton comprises a first connection member, a second connection member, a first joint member, a second joint member, a first fixing structure, a second fixing structure, a third fixing structure, a first sensor and a first controller. The first connection member and the second connection member are connected by the second joint member, the first fixing structure and the first connection member are connected by the first joint member, the second fixing member is connected to the first connection member, and the third fixing structure is connected to the second connection member.

In addition, the first fixing structure is fixed at a waist of the user, so as to fix the first joint member at the waist of the user. The second fixing structure is fixed at a thigh of the user, so as to fix the first connection member at the thigh of the user. The third fixing structure is fixed at a shank of the user, so as to fix the second connection member at the shank of the user. Alternatively, the fixing structure is a bandage. Of course, the fixing structure may also be other fixed molding and ergonomic structures, such as a metal or plastic snap. Accordingly in the present embodiment, the first joint member, the first connection member and the second connection member are fixed at corresponding parts of the user's body by the bandages.

The control method of the power exoskeleton includes step 1001 and step 1002.

In step 1001, the first sensor obtains a motion state parameter of an arm of the user.

In the present embodiment, before the step of obtaining, by the first sensor, the motion state parameter of the arm of the user, the control method includes: enabling the arm of the user to keep natural prolapse for a predetermined time, so as to initialize the wearable device. The first controller provided by the present embodiment may further be used for controlling to enable and disable the power exoskeleton. Before the user who wears the power exoskeleton starts to act, the power exoskeleton is enabled by the first controller, and at the same time, two arms are kept natural prolapse for at least no less than one second, guaranteeing that the power exoskeleton is enabled normally.

In step 1002, the first controller controls, according to the motion statement parameter, the first connection member and the second connection member to act, so as to drive the thigh and the shank to act.

In the present embodiment, the first sensor includes at least one of an acceleration meter, a data processor and an angle meter. The step of obtaining, by the first sensor, the motion state parameter of the arm of the user includes:

measuring, by the acceleration meter, an angle acceleration between the upper arm and a middle axis of body; calculating, by the data processor, the swing amplitude and the swing frequency of the arm according to the angle acceleration; and measuring, by the angle meter, the elbow joint angle between the upper arm and the forearm. The first sensors are fixed at the elbow joints of left and right sides of the body, the acceleration meter may be an accelerometer or a gyroscope, and the angle meter may be a tension meter for measuring the angle between the upper arm and the forearm. A magnitude of the tension generated when the elbow joint is bent reflects a bending degree of the elbow joint, i.e., the elbow joint angle. Alternatively, the first sensor further includes a radio module for transmitting measurement information to the first controller, the measurement information including the swing amplitude, the swing frequency and the elbow joint angle.

With reference to FIG. 4, the swing amplitude of the power exoskeleton is represented as a first angle $\alpha$. The first angle $\alpha$ is an angle formed between the upper arm and a middle axis of body when the arm swings forward or backward. With reference to FIG. 5, the elbow joint angle of the power exoskeleton is represented as a second angle $\beta$. The second angle $\beta$ is an angle between the upper arm and the forearm when the elbow angle is bent.

Figure 7:
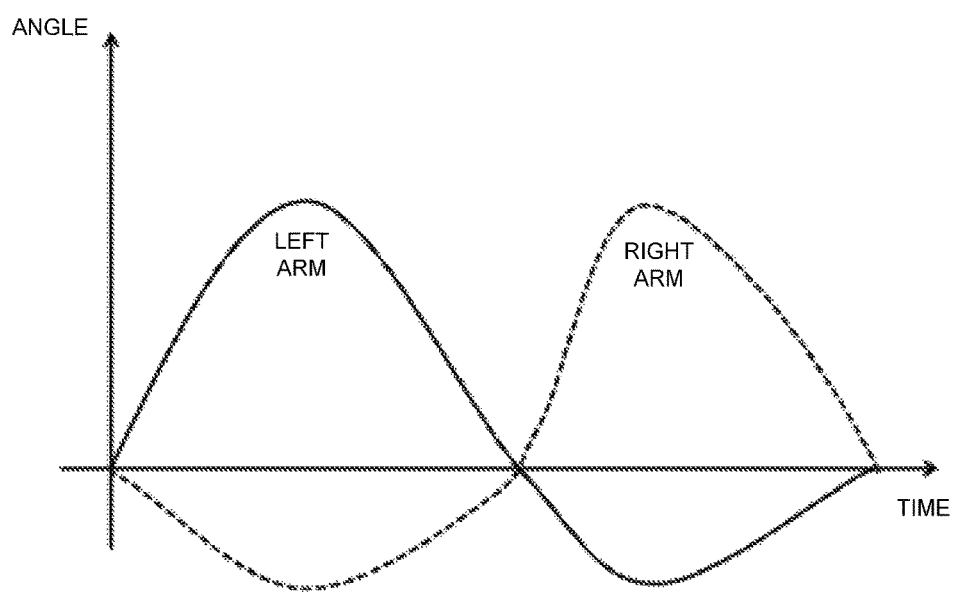
FIG. 7 is a schematic diagram illustrating first angles between a left arm and a right arm in the second embodiment of the present disclosure.

FIG. 7 is a schematic diagram illustrating first angles between a left arm and a right arm in the second embodiment of the present disclosure. As shown in FIG. 7, a solid line represents a motion of the left arm, the left arm firstly swinging forward, and then swinging backward. A dotted line represents a motion of the right arm, the right arm firstly swinging backward, and then swinging forward. In particular, the sensor obtains the angle acceleration between the upper arm and the middle axis of the body, and then integrates the time, so as to obtain a relationship between the angle and the time. Within one cycle of dual-arm swinging, an amplitude of the swinging forward is larger than an amplitude of the swinging backward, and respective smooth curves may be obtained by data processing, wherein in a process of swinging forward, the swing amplitude of the left arm is $\alpha_{Li}$, the swing amplitude of the right arm is $\alpha_{Ri}$, and i represents a cycle number.

In the present embodiment, the arm of the user is in a periodical motion state, and the step of controlling, by the first controller according to the motion statement parameter, the first connection member and the second connection member to act includes: controlling, by the first controller according to the motion statement parameter of the arm of the user after at least one motion cycle, the first connection member and the second connection member to act, so as to enable actions of the thigh and the shank to be delayed by at least one motion cycle relative to the action of the arm. Therefore, in the walking process, the motion time period of lower limbs is delayed by at least one motion cycle relative to that of upper limbs. Particularly, when i=0, the upper limbs move to enable the power exoskeleton, while the lower limbs are kept still. When the lower limbs begin to move, the motion state parameter of the i-th cycle period of the lower limbs movement is determined by the motion state parameter of the (i−1)-th cycle period of the upper limbs movement, so that the actions of the thighs and the shanks are delayed by at least one motion cycle relative to the actions of the arms, and thus security performance may be improved.

In the present embodiment, the power exoskeleton further includes a foot support member, a third joint member and a fourth fixing structure. The foot support member is connected to the second connection member by the third joint member, and the fourth fixing structure is connected to the foot support member. The fourth fixing structure is used to be fixed at a foot of the user, so as to fix the foot support member at the foot of the user. The control method further includes: controlling, by the first controller according to the motion state parameter, the foot support member to act, so as to drive the foot to act. In actual applications, the foot support member may also be fixed at the foot of the user by the bandage. Of course, the fixing structure for fixing the foot support member at the user's foot may also be other fixed molding and ergonomic structures, such as a metal or plastic snap.

Preferably, the step of obtaining, by the first sensor, the motion state parameter of the arm of the user includes: obtaining, by the first sensor, a swing amplitude of the arm and an elbow joint angle between an upper arm and a forearm. The step of controlling, by the first controller according to the motion statement parameter, the first connection member and the second connection member to act includes: determining whether the swing amplitude is larger than a first predetermined threshold; determining whether the elbow joint angle is larger than a second predetermined threshold, if the swing amplitude is larger than the first predetermined threshold; controlling, by the first controller, the first connection member and the second connection member to act so as to enable the user to be in a walking mode, if the elbow joint angle is smaller than the second predetermined threshold; and controlling, by the first controller, the first connection member and the second connection member to act so as to enable the user to be in a running mode, if the elbow joint angle is larger than the second predetermined threshold.

In actual applications, before the power exoskeleton is enabled, if $\alpha_0 > \alpha_S$ is detected, the power exoskeleton is enabled, and simultaneously it is determined whether the elbow joint angle is larger than the second predetermined threshold, wherein $\alpha_0$ is the swing amplitude of the arm before the power exoskeleton is enabled, and $\alpha_S$ is the first predetermined threshold. If $\alpha_0 < \alpha_S$ is detected, the power exoskeleton is not enabled, wherein $\alpha_0$ is the swing amplitude of the arm before the power exoskeleton is enabled, and $\alpha_S$ is the first predetermined threshold.

Preferably, the step of obtaining, by the first sensor, the motion state parameter of the arm of the user includes: obtaining, by the first sensor, a first swing amplitude of a left arm, a second swing amplitude of a right arm and an elbow joint angle between an upper arm and a forearm. In addition, the step of controlling, by the first controller according to the motion statement parameter, the first connection member and the second connection member to act includes: determining whether the first swing amplitude is larger than a first predetermined threshold, whether the second swing amplitude is larger than the first predetermined threshold, and whether a dual-arm coordination degree is smaller than a third predetermined threshold, the dual-arm coordination degree being an absolute value of a difference between the first swing amplitude and the second swing amplitude; determining whether the elbow joint angle is larger than a second predetermined threshold, if the first swing amplitude is larger than the first predetermined threshold, the second swing amplitude is larger than the first predetermined threshold, and the dual-arm coordination degree is smaller than the third predetermined threshold; controlling, by the first controller, the first connection member and the second connection member to act so as to enable the user to be in a walking mode, if the elbow joint angle is smaller than the second predetermined threshold; and controlling, by the first controller, the first connection member and the second connection member to act so as to enable the user to be in a running mode, if the elbow joint angle is larger than the second predetermined threshold.

In actual applications, before the power exoskeleton is enabled, it is required that $|\alpha_{L0}-\alpha_{R0}|<\alpha_{sf}$, $\alpha_{L0}>\alpha_S$ and $\alpha_{R0}>\alpha_S$, wherein $\alpha_{L0}$ is the swing amplitude of the left arm before the power exoskeleton is enabled, $\alpha_{R0}$ is the swing amplitude of the right arm before the power exoskeleton is enabled, $|\alpha_{L0}-\alpha_{R0}|$ is a dual-arm coordination degree, $\alpha_{sf}$ is the third predetermined threshold, $\alpha_S$ is the first predetermined threshold. The third predetermined threshold is a safe threshold, and the less the safe threshold is, the more difficulty the power exoskeleton acts. When the swing amplitudes of the left and the right arms are similar, the power exoskeleton starts to act. When the dual-arm coordination degree equals to zero, it represents that the swing amplitudes of the two arms are completely identical.

Alternatively, during the power exoskeleton is in the walking process, the step length of the lower limbs in the i-th motion cycle is $STEP\alpha_i=K\alpha_i*STEP\alpha_M$, in which a proportion coefficient $K\alpha_i=(\alpha_{L(i-1)}+\alpha_{R(i-1)})/(2\alpha_M)$, $\alpha_{L(i-1)}$ is the first swing amplitude of the left arm in the (i−1)-th motion cycle, $\alpha_{R(i-1)}$ is the second swing amplitude of the right arm in the (i−1)-th motion cycle, $\alpha_M$ is a predetermined maximum swing amplitude of the upper limbs, $STEP\alpha_M$ is a predetermined maximum step length of the lower limbs. When the obtained proportion coefficient $K\alpha_i$ is larger than 1, the proportion coefficient $K\alpha_i$ is set to be 1 so that the proportion coefficient $K\alpha_i$ is no more than 1.

Alternatively, during the power exoskeleton is in the walking process, the frequency of the lower limbs in the i-th motion cycle is $STEP\gamma i=K\gamma i*STEP\gamma M$, in which a proportion coefficient $K\gamma i=(\gamma_{L(i-1)}+\gamma_{R(i-1)})/(2\gamma_M)$, $\gamma L(i-1)$ is the first swing frequency of the left arm in the (i−1)-th motion cycle, $\gamma_{R(i-1)}$ is the second swing frequency of the right arm in the (i−1)-th motion cycle, $\gamma_M$ is a predetermined maximum swing frequency of the upper limbs, $STEP\gamma_M$ is the predetermined maximum frequency of the lower limbs. When the obtained proportion coefficient $K\gamma_i$ is larger than 1, the proportion coefficient $K\gamma_i$ is set to be 1 so that the proportion coefficient $K\gamma_i$ is no more than 1.

When the power exoskeleton is enabled, if $\beta_i<\beta_s$, is detected, the power exoskeleton enters the walking mode, in which $\beta_i$ represents the elbow joint angle between the upper arm and the forearm in the i-th motion cycle, and $\beta_s$ is the second predetermined threshold. If $\beta_i>\beta_s$ is detected, the power exoskeleton enters the running mode, in which $\beta_i$ represents the elbow joint angle between the upper arm and the forearm in the i-th motion cycle, and $\beta_s$ is the second predetermined threshold. Measuring the elbow joint angle between the upper arm and the forearm may be implemented by the angle meter. The angle meter measures an angle variation of the upper arm relative to the human body axis, and then measures an angle variation of the forearm relative to the human body axis, their difference being the elbow joint angle between the upper arm and the forearm.

In the walking mode, the power exoskeleton acts based on a preset human walking gait cycle. For example, the first driver rotates forward to raise the thigh, the second driver rotates backward to bring the shank to be vertical to the ground, and the third driver rotates to cause a sole of foot from contacting the ground by a tiptoe to contacting the ground by the whole sole, or from leaving the ground by a heel to leaving the ground by the whole sole.

In the running mode, the rotation angle and the angle acceleration of the respective joint drivers preset by the power exoskeleton are larger than those in the walking mode. The running mode differs from the walking mode in that the swing amplitude and the swing frequency in the running mode are larger, and the sole does not contact the ground completely with a rising time. Taking the security into consideration, the above two modes are set with corresponding maximum thresholds. The swing amplitude and the swing frequency which are beyond the maximum thresholds will be performed with the swing amplitude and the swing frequency at the maximum thresholds. When the user enters a stop state from the motion state, the power exoskeleton will immediately be restored to a state in which two legs are standing normally, no matter which of the states the power exoskeleton is in.

In the control method of the power exoskeleton provided by the present embodiment, the power exoskeleton includes a first connection member, a second connection member, a first joint member, a second joint member, a first fixing structure, a second fixing structure, a third fixing structure, a first sensor and a first controller. The first sensor obtains the motion state parameter of the arm of the user; the first controller controls, according to the motion statement parameter, the first connection member and the second connection member to act, so as to drive the thigh and the shank to act. In the present embodiment, the motion state parameter of the arm of the user is obtained; and according to the motion state parameter, the first connection member and the second connection member are controlled to act for implementing motion control, so that the user can adjust his walking speed and stride naturally and conveniently. The technical solution provided by the embodiment has a simple structure, requires a lower demand on operation capability of the user, and has higher operation flexibility. In addition, the technical solution provided by the present embodiment may be applied to the user whose lower limbs completely lose their movement functions, as long as the arms of the user have normal functions, which thus have a broader application range.

The above are merely the preferred embodiments of the present disclosure and shall not be used to limit the scope of the present disclosure. It should be noted that, a person skilled in the art may make improvements and modifications without departing from the principle of the present disclosure, and these improvements and modifications shall also fall within the scope of the present disclosure.

What is claimed is:

1. A wearable device for enhancing physical fitness, which comprises a first connection member, a second connection member, a first joint member, a second joint member, a first fixing structure, a second fixing structure, a third fixing structure, a first sensor and a first controller, the first connection member and the second connection member being connected by the second joint member, the first fixing structure and the first connection member being connected by the first joint member, the second fixing member being connected to the first connection member, and the third fixing structure being connected to the second connection member;

wherein the first fixing structure is used to be fixed at a waist of a user so as to fix the first joint member at the waist of the user;

the second fixing structure is used to be fixed at a thigh of the user so as to fix the first connection member at the thigh of the user;

the third fixing structure is used to be fixed at a shank of the user so as to fix the second connection member at the shank of the user;

the first sensor is used to obtain a motion state parameter of an arm of the user; and the first controller is used to control, according to the motion statement parameter, the first connection member and the second connection member to act, so as to drive the thigh and the shank to act;

wherein the motion state parameter comprises a swing amplitude of the arm and an elbow joint angle between an upper arm and a forearm.

2. The wearable device according to claim 1, wherein the wearable device is power exoskeleton.

3. The wearable device according to claim 1, wherein the motion state parameter further comprises a swing frequency of the arm.

4. The wearable device according to claim 1, wherein the first connection member comprises a thigh connection rod, and the second connection member comprises a shank connection rod.

5. The wearable device according to claim 1, wherein the first joint member comprises a first driver and a hip joint, and the second joint member comprises a second driver and a knee joint.

6. The wearable device according to claim 3, wherein the first sensor comprises at least one of an acceleration meter, a data processor and an angle meter;

the acceleration meter is used to measure an angle acceleration between the upper arm and a middle axis of body;

the data processor is used to calculate the swing amplitude and the swing frequency of the arm according to the angle acceleration; and the angle meter is used to measure the elbow joint angle between the upper arm and the forearm.

7. The wearable device according to claim 1, wherein the first sensor is arranged at the elbow joint of the user.

8. A method for controlling a wearable device, the wearable device being used for enhancing physical fitness and comprising a first connection member, a second connection member, a first joint member, a second joint member, a first fixing structure, a second fixing structure, a third fixing structure, a first sensor and a first controller, the first connection member and the second connection member being connected by the second joint member, the first fixing structure and the first connection member being connected by the first joint member, the second fixing member being connected to the first connection member, and the third fixing structure being connected to the second connection member;

wherein the first fixing structure is used to be fixed at a waist of a user so as to fix the first joint member at the waist of the user;

the second fixing structure is used to be fixed at a thigh of the user so as to fix the first connection member at the thigh of the user;

the third fixing structure is used to be fixed at a shank of the user so as to fix the second connection member at the shank of the user;

the method comprising:

obtaining, by the first sensor, a motion state parameter of an arm of the user; and controlling, by the first controller according to the motion statement parameter, the first connection member and the second connection member to act, so as to drive the thigh and the shank to act;

wherein the step of obtaining, by the first sensor, the motion state parameter of the arm of the user comprises:

obtaining, by the first sensor, a swing amplitude of the arm and an elbow joint angle between an upper arm and a forearm;

wherein the step of controlling, by the first controller according to the motion statement parameter, the first connection member and the second connection member to act comprises:

determining whether the swing amplitude is larger than a first predetermined threshold;

determining whether the elbow joint angle is larger than a second predetermined threshold, if the swing amplitude is larger than the first predetermined threshold;

controlling, by the first controller, the first connection member and the second connection member to act so as to enable the user to be in a walking mode, if the elbow joint angle is smaller than the second predetermined threshold; and controlling, by the first controller, the first connection member and the second connection member to act so as to enable the user to be in a running mode, if the elbow joint angle is larger than the second predetermined threshold.

9. The method according to claim 8, wherein the wearable device is power exoskeleton.

10. The method according to claim 8, wherein when the arm of the user is in a periodical motion state, the step of controlling, by the first controller according to the motion statement parameter, the first connection member and the second connection member to act comprises:

controlling, by the first controller according to the motion statement parameter of the arm of the user after at least one motion cycle, the first connection member and the second connection member to act, so as to enable actions of the thigh and the shank to be delayed by at least one motion cycle relative to the action of the arm.

11. The method according to claim 8, wherein before the step of obtaining, by the first sensor, the motion state parameter of the arm of the user, the method further comprises:

enabling the arm of the user to keep natural prolapse for a predetermined time, so as to initialize the wearable device.

12. The method according to claim 8, wherein the motion state parameter further comprises a swing frequency of the arm and the first sensor comprises at least one of an acceleration meter, a data processor and an angle meter; and the step of obtaining, by the first sensor, the motion state parameter of the arm of the user comprises:

measuring, by the acceleration meter, an angle acceleration between the upper arm and a middle axis of body;

calculating, by the data processor, the swing amplitude and the swing frequency of the arm according to the angle acceleration; and measuring, by the angle meter, the elbow joint angle between the upper arm and the forearm.

13. A method for controlling a wearable device, the wearable device being used for enhancing physical fitness and comprising a first connection member, a second connection member, a first joint member, a second joint member, a first fixing structure, a second fixing structure, a third fixing structure, a first sensor and a first controller, the first connection member and the second connection member being connected by the second joint member, the first fixing structure and the first connection member being connected by the first joint member, the second fixing member being connected to the first connection member, and the third fixing structure being connected to the second connection member;

wherein the first fixing structure is used to be fixed at a waist of a user so as to fix the first joint member at the waist of the user;

the second fixing structure is used to be fixed at a thigh of the user so as to fix the first connection member at the thigh of the user;

the third fixing structure is used to be fixed at a shank of the user so as to fix the second connection member at the shank of the user;

the method comprising:

obtaining, by the first sensor, a motion state parameter of an arm of the user; and controlling, by the first controller according to the motion statement parameter, the first connection member and the second connection member to act, so as to drive the thigh and the shank to act;

wherein the step of obtaining, by the first sensor, the motion state parameter of the arm of the user comprises:

obtaining, by the first sensor, a first swing amplitude of a left arm, a second swing amplitude of a right arm and an elbow joint angle between an upper arm and a forearm;

wherein the step of controlling, by the first controller according to the motion statement parameter, the first connection member and the second connection member to act comprises:

determining whether the first swing amplitude is larger than a first predetermined threshold, whether the second swing amplitude is larger than the first predetermined threshold, and whether a dual-arm coordination degree is smaller than a third predetermined threshold, the dual-arm coordination degree being an absolute value of a difference between the first swing amplitude and the second swing amplitude;

determining whether the elbow joint angle is larger than a second predetermined threshold, if the first swing amplitude is larger than the first predetermined threshold, the second swing amplitude is larger than the first predetermined threshold, and the dual-arm coordination degree is smaller than the third predetermined threshold;

controlling, by the first controller, the first connection member and the second connection member to act so as to enable the user to be in a walking mode, if the elbow joint angle is smaller than the second predetermined threshold; and controlling, by the first controller, the first connection member and the second connection member to act so as to enable the user to be in a running mode, if the elbow joint angle is larger than the second predetermined threshold.

14. The method according to claim 13, wherein the wearable device is power exoskeleton.

15. The method according to claim 13, wherein when the arm of the user is in a periodical motion state, the step of controlling, by the first controller according to the motion statement parameter, the first connection member and the second connection member to act comprises:

controlling, by the first controller according to the motion statement parameter of the arm of the user after at least one motion cycle, the first connection member and the second connection member to act, so as to enable actions of the thigh and the shank to be delayed by at least one motion cycle relative to the action of the arm.

16. The method according to claim 13, wherein before the step of obtaining, by the first sensor, the motion state parameter of the arm of the user, the method further comprises:

enabling the arm of the user to keep natural prolapse for a predetermined time, so as to initialize the wearable device.

17. The method according to claim 13, wherein the motion state parameter further comprises a swing frequency of the arm and the first sensor comprises at least one of an acceleration meter, a data processor and an angle meter; and the step of obtaining, by the first sensor, the motion state parameter of the arm of the user comprises:

measuring, by the acceleration meter, an angle acceleration between the upper arm and a middle axis of body;

calculating, by the data processor, the swing amplitude and the swing frequency of the arm according to the angle acceleration; and measuring, by the angle meter, the elbow joint angle between the upper arm and the forearm.

* * * * *